(12) United States Patent
Blanz et al.

(10) Patent No.: US 9,671,483 B2
(45) Date of Patent: Jun. 6, 2017

(54) T2 INVERSIONS WITH REDUCED MOTION ARTIFACTS

(71) Applicants: Martin Blanz, Celle (DE); Holger Frank Thern, Hannover (DE); Radu Coman, Hannover (DE)

(72) Inventors: Martin Blanz, Celle (DE); Holger Frank Thern, Hannover (DE); Radu Coman, Hannover (DE)

(73) Assignee: BAKER HUGHES INCORPORATED, Houston, TX (US)

(*) Notice: Subject to any disclaimer, the term of this patent is extended or adjusted under 35 U.S.C. 154(b) by 580 days.

(21) Appl. No.: 14/190,337

(22) Filed: Feb. 26, 2014

(65) Prior Publication Data

US 2015/0241541 A1    Aug. 27, 2015

(51) Int. Cl.

| | |
|---|---|
| *G01V 3/00* | (2006.01) |
| *G01R 33/565* | (2006.01) |
| *G01V 3/32* | (2006.01) |
| *G01V 3/38* | (2006.01) |
| *G01N 24/08* | (2006.01) |
| *G01R 33/44* | (2006.01) |

(52) U.S. Cl.
CPC ..... *G01R 33/56509* (2013.01); *G01N 24/081* (2013.01); *G01R 33/448* (2013.01); *G01V 3/32* (2013.01); *G01V 3/38* (2013.01)

(58) Field of Classification Search
USPC .......................................................... 324/303
See application file for complete search history.

(56) References Cited

U.S. PATENT DOCUMENTS

| | | | | |
|---|---|---|---|---|
| 5,428,291 A | * | 6/1995 | Thomann | G01N 15/08 324/303 |
| 6,046,587 A | * | 4/2000 | King | E21B 47/102 324/306 |
| 6,069,477 A | | 5/2000 | Chen et al. | |

(Continued)

OTHER PUBLICATIONS

Notification of Transmittal of the International Search Report and the Written Opinion of the International Searching Authority, or the Declaration; PCT/US2015/017276; Mailed May 29, 2015, 11 pages.

(Continued)

*Primary Examiner* — Rodney Fuller
(74) *Attorney, Agent, or Firm* — Cantor Colburn LLP

(57) ABSTRACT

A method for processing nuclear magnetic resonance (NMR) measurement data includes: receiving, with a processor, NMR measurement data obtained from an NMR tool, the NMR measurement data being affected by a motion artifact and having a first echo train obtained with a long polarization time $TW_{ET}$ and a second echo train obtained with a short polarization time $TW_{TL}$ that is shorter than $TW_{ET}$; and at least one of (i) reducing, with a processor, an effect on the NMR measurement data of the motion artifact using the first echo train and the second echo train and (ii) identifying, with a processor, the motion artifact using the first echo train and the second echo train; wherein the motion artifact is related to a magnetic field magnitude that varies in a volume of interest due to a motion of the NMR tool.

22 Claims, 11 Drawing Sheets

(56) References Cited

U.S. PATENT DOCUMENTS

| | | | |
|---|---|---|---|
| 6,566,874 B1 * | 5/2003 | Speier | G01V 3/32 |
| | | | 324/303 |
| 7,180,287 B2 | 2/2007 | Rottengatter et al. | |
| 7,268,547 B2 | 9/2007 | Kruspe et al. | |
| 7,812,602 B2 * | 10/2010 | Edwards | G01N 24/081 |
| | | | 324/303 |
| 2001/0043066 A1 * | 11/2001 | Hawkes | G01V 3/32 |
| | | | 324/303 |
| 2003/0006769 A1 | 1/2003 | Edwards | |
| 2005/0088176 A1 * | 4/2005 | Kruspe | G01V 3/32 |
| | | | 324/303 |
| 2005/0248342 A1 | 11/2005 | Rottengatter et al. | |
| 2006/0033491 A1 * | 2/2006 | Blanz | G01N 24/081 |
| | | | 324/303 |
| 2007/0222443 A1 | 9/2007 | Blanz | |
| 2007/0241750 A1 | 10/2007 | Akkurt | |
| 2014/0077813 A1 * | 3/2014 | Holmes | G01R 33/4824 |
| | | | 324/322 |
| 2015/0309146 A1 * | 10/2015 | Jin | G01R 33/56509 |
| | | | 324/309 |

OTHER PUBLICATIONS

K. J. Dunn, D. J. Bergman, G. A. LaTorraca, S. M. Stonard, and M. B. Crowe; "A Method for Inverting NMR Data Sets With Different Signal to Noise Ratios"; SPWLA 39th Annual Logging Symposium, May 26-29, 1998; 11 pages.

* cited by examiner

| Relaxation and inversion type | Total | 0-3.3 ms | 3.3-100 ms | 0.1-4 s | R=T1/T2 | Amot | Tmot | Comment |
|---|---|---|---|---|---|---|---|---|
| | [%] | [%] | [%] | [%] | | | [S] | |
| Input data FF | 100 | 0 | 0 | 100 | 1.5 | – | – | *True FF data without motion.* |
| JI | 95.1 | – | 7.1 | 88.0 | 3.2 | – | – | *Prior art JI* → too much BW, too high R. |
| JIMC | 99.9 | 0.0 | 0.2 | 99.7 | 1.9 | 0.13 | 0.03 | Small motion correction with still rather high R. |
| Input Data SS | 100 | 10 | 30 | 60 | 1.5 | – | – | *True SS data without motion.* |
| JI, one trainlet TW = 60 ms | 102.0 | 9.9 | 40.6 | 51.6 | 2.7 | – | – | *Prior art JI* → too much BW, too high R. |
| JIMC, one trainlet TW = 60 ms | 102.0 | 9.9 | 40.2 | 51.8 | 2.6 | 0.000004 | 0.13 | Motion correction can be improved. Same result as with prior art JI. |
| JIMC, two trainlets | 101.0 | 10.9 | 29.7 | 60.4 | 1.4 | 0.16 | 0.04 | Excellent motion correction with two trainlets. |

FIG.13

T2 INVERSIONS WITH REDUCED MOTION ARTIFACTS

BACKGROUND

Earth formations, or simply formations, may be used for various purposes such as hydrocarbon production, geothermal production, and carbon dioxide sequestration. In order to make optimal use of a formation, it is typically characterized using a downhole tool that is conveyed through a borehole penetrating the formation.

One type of downhole tool is a nuclear magnetic resonance (NMR) tool that performs NMR measurements on the formation to determine various properties such as porosity for example. In one application referred to as logging-while-drilling, the NMR tool is coupled to a drill string. The NMR tool performs NMR measurements while the drill string is rotating causing a drill bit also coupled to the drill string to drill the borehole. The drill process, however, may cause the drill string to move laterally in the borehole thus continuously varying the distance from the NMR tool to the formation being characterized. Lateral motion of the NMR tool may also occur due to rotation of the tool without drilling. Unfortunately, the continuously varying distance may induce motion artifacts in the obtained NMR data resulting in a decrease in the accuracy of the data.

BRIEF SUMMARY

Disclosed is a method for processing nuclear magnetic resonance (NMR) measurement data. The method includes: receiving, with a processor, NMR measurement data obtained from an NMR tool, the NMR measurement data being affected by a motion artifact and having a first echo train obtained with a long polarization time $TW_{ET}$ and a second echo train obtained with a short polarization time $TW_{TL}$ that is shorter than $TW_{ET}$; and at least one of (i) reducing, with a processor, an effect on the NMR measurement data of the motion artifact using the first echo train and the second echo train and (ii) identifying, with a processor, the motion artifact using the first echo train and the second echo train; wherein the motion artifact is related to a magnetic field magnitude that varies in a volume of interest due to a motion of the NMR tool.

Also disclosed is a method for performing nuclear magnetic resonance (NMR) measurements on an earth formation. The method includes: conveying an NMR tool through a borehole penetrating the earth formation; receiving, with a processor, NMR measurement data obtained from the NMR tool disposed on the carrier, the NMR measurement data being affected by a motion artifact and having a first echo train obtained with a long polarization time $TW_{ET}$ and a second echo train obtained with a short polarization time $TW_{TL}$ that is shorter than $TW_{ET}$; and at least one of (i) reducing, with a processor, an effect on the NMR measurement data of the motion artifact using the first echo train and the second echo train and (ii) identifying, with a processor, the motion artifact using the first echo train and the second echo train; wherein the motion artifact is related to a magnetic field magnitude that varies in a volume of interest due to a motion of the NMR tool.

BRIEF DESCRIPTION OF THE DRAWINGS

The following descriptions should not be considered limiting in any way. With reference to the accompanying drawings, like elements are numbered alike:

FIG. 13 presets tabled results of numerical examples; and

DETAILED DESCRIPTION

A detailed description of one or more embodiments of the disclosed apparatus and method presented herein by way of exemplification and not limitation with reference to the figures.

Disclosed are method and apparatus for processing measurements performed by a nuclear magnetic resonance (NMR) tool that may be subject to motion in a borehole. Alternatively or in combination with tool motion, the NMR tool may have a non-axially symmetric magnetic field such that when the tool is rotated, the magnetic field magnitude varies at a fixed location in the formation. The motion may cause the NMR measurements to inaccurately quantify properties of the formation. The inaccuracy induced into the NMR measurements due to the motion (or non-axially symmetric magnetic field motion) is called a motion artifact. The processing techniques disclosed herein identify a motion artifact and remove it from the NMR measurement data to provide corrected NMR measurement data that more accurately quantify properties of the formation.

Figure 1:
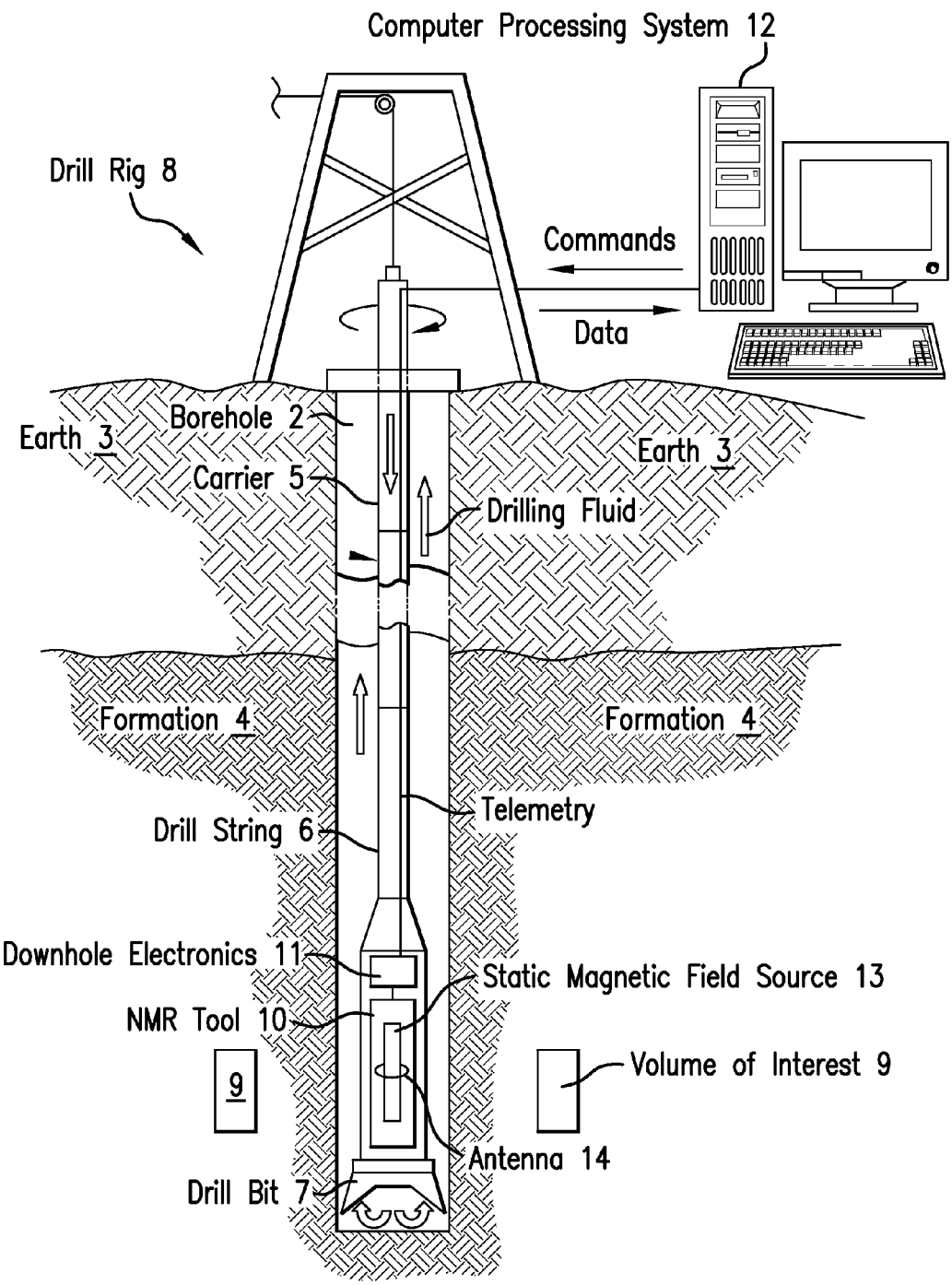
FIG. 1 illustrates a cross-sectional view of an exemplary embodiment of a nuclear magnetic resonance (NMR) tool disposed in a borehole penetrating the earth.

Next apparatus for implementing the teachings herein is discussed. FIG. 1 illustrates a cross-sectional view of an exemplary embodiment of an NMR tool 10 disposed in a borehole 2 penetrating the earth 3, which includes an earth formation 4. The NMR tool 10 is configured to perform NMR measurements on the formation 4. The NMR measurements include generating NMR signal echoes from atomic nuclei, such as hydrogen nuclei, of the formation. Long echo trains can be recorded. The decays of the echo trains are caused by the so-called $T_2$ relaxation, also known as transverse or spin-spin relaxation. The NMR measurements yield transverse relaxation times $T_2$, which are exponential decay time constants that correspond to a characteristic or property of the formation 4 material. Transverse relaxation relates to the loss of phase coherence of the protons in the formation 4 material while precessing about a static magnetic field during an NMR measurement. There is not one single value of $T_2$ for formation fluids but a wide distribution of values lying anywhere between fractions of a millisecond and several seconds for example. The quantitative distribution of $T_2$ values is the principal output of the NMR tool 10. A sequence of T2 distribution plotted versus depth in the borehole may be referred to as an NMR T2 distribution log. The NMR tool 10 may also output longitudinal relaxation time constants ($T_1$) associated with polarizing the nuclei in the formation.

The $T_2$ (also referred to as T2) decay may be approximated by a sum of exponential functions (multi-exponential approximation) resulting in a T2 distribution. The process of obtaining this T2 distribution is commonly called T2 inversion, echo fit or mapping. From the T2 distribution, total porosity, partial porosities, pore size and fluid type in the formation may be determined—properties that are of particular interest. The long T2 components are usually called Free Fluid (FF) components or Bulk Volume Moveable (BVM); the medium T2 components are usually called Bound Water (BW) components or Bulk Volume Irreducible (BVI); and the short T2 components are usually called Clay Bound Water (CBW) components.

The basic NMR method for obtaining the T2 echo decay is a long wait time ($TW_{long}$, polarization time) to get close to (or achieve full) equilibrium polarization, followed by a train of several hundred to several thousand NMR echoes generated, for example, by a pulse echo sequence such as the well-known Carr Purcell Meiboom Gill (CPMG) pulse echo sequence. The equilibrium polarization is useful to get the total porosity from the start amplitude of the echo train. In addition to the long echo train with long TW, echo trains with short $TW_{short}$ (called trainlets or bursts) are used for a more accurate determination of the short T2 components in the T2 distribution. Usually, but not necessarily, the trainlets are shorter (i.e., they have a smaller number of echoes) than the long echo train with long $TW_{long}$.

In one or more embodiments, a number of NMR echo trains (with long TW) are acquired and averaged. Preferably TW being long enough to polarize all NMR components fully. A number of NMR trainlets (with short TW) are acquired and averaged. Usually the trainlets have a small number of echoes only (to save time, memory and power) and use a short TW (in the prior art: to save time and consequently increase signal-to-noise ratio (SNR) of the measurement; in the present disclosure to reduce motion artifacts). The trainlet TW should be long enough to polarize fully the T2 components that are later, after inversion, extracted from the trainlet T2 distribution. The number of averaged trainlets is greater than the number of averaged echo trains with long TW in order to get a better determination of the short T2 components. These acquired data may be processed (i.e., inverted) according to an inversion method such as one of those discussed below.

Components in the NMR tool 10 includes a static magnetic field source 13 that magnetizes formation materials and an antenna 14 that transmits precisely timed bursts of radio-frequency energy that provides an oscillating magnetic field. In a time period between these pulses, the antenna receives a decaying echo signal from those hydrogen protons that are in resonance with the static magnetic field produced by the static magnetic field source at the transmitted RF frequency. NMR measurements are performed in a toroidal volume surrounding the NMR tool 10 referred to as a volume of interest 9. Because a linear relationship exists between the proton resonance frequency and the strength of the static magnetic field, the frequency of transmitted radio-frequency energy can be tuned to match the static magnetic field in the volume of interest. It can be appreciated that the NMR tool 10 may include a variety of components and configurations as known in the art of NMR. In that NMR tools are known in the art, specific details of components and configurations of these tools are not discussed in further detail.

The NMR tool 10 is conveyed through the borehole 2 by a carrier 5, which can be a drill tubular such as a drill string 6. A drill bit 7 is disposed at the distal end of the drill string 6. A drill rig 8 is configured to conduct drilling operations such as rotating the drill string 6 and thus the drill bit 7 in order to drill the borehole 2. In addition, the drill rig 8 is configured to pump drilling mud (i.e., drill fluid) through the drill string 6 in order to lubricate the drill bit 7 and flush cuttings from the borehole 2. Downhole electronics 11 are configured to operate the NMR tool 10, process measurement data obtained downhole, and/or act as an interface with telemetry to communicate data or commands between downhole components and a computer processing system 12 disposed at the surface of the earth 3. Non-limiting embodiments of the telemetry include pulsed-mud and wired drill pipe for real time communications. System operation and data processing operations may be performed by the downhole electronics 11, the computer processing system 12, or a combination thereof. In an alternative embodiment, the carrier 5 may be an armored wireline, which may also provide communications with the surface processing system 12.

Next, T2 inversions that combine long echo trains and trainlets are discussed. There are several known methods of inversion that may be used to achieve this. See for example variants of Separate Inversion (SI) (also called splicing technique) and Joint Inversion (JI) (also called composite-data processing) in A METHOD FOR INVERTING NMR DATA SETS WITH DIFFERENT SIGNAL TO NOISE RATIOS, K. J. Dunn, D. J. Bergman, G. A. LaTorraca, S. M. Stonard, and M. B. Crowe; SPWLA 39$^{th}$ Annual Logging Symposium, May 26-29, 1998. That paper is called REF1 in this disclosure.

In the joint inversion (JI) technique, the multi-exponential approximation equations for the measured data may be represented as:

$$EET_i = \sum_k \left( \phi_k \cdot e^{-\frac{t_i}{T2_k}} \cdot \left(1 - e^{-\frac{TW_{ET}}{R \cdot T2_k}}\right) \right) \quad (1)$$

$$ETL_j = \sum_k \left( \phi_k \cdot e^{-\frac{t_j}{T2_k}} \cdot \left(1 - e^{-\frac{TW_{TL}}{R \cdot T2_k}}\right) \right)$$

where $EET_i$ is the $i^{th}$ echo amplitude at time $t_i$ of the long echo train with a long wait time $TW_{ET}$, and $ETL_j$ is the $j^{th}$ echo amplitude at time $t_j$ of a trainlet with a short wait time $TW_{TL}$. $\phi_k$'s are the sought-after T2 components of the T2 distribution i.e., the amplitudes of the exponential functions associated with chosen fixed $T2_k$ (or $T2_k$ bins—selected intervals into which T2's are categorized) where k runs from 1 to the chosen number of T2 bins. The $\phi_k$'s are optimized during the inversion process to achieve the best fit to the measured NMR data. The range of i runs from 1 to the number of echoes of the long echo train, while the range of j runs from 1 to the number of trainlet echoes. Ideally, $TW_{ET}$ should be long enough (e.g. $>5*T_1$), where $T_1$ is the longest $T_1$ component of the formation, to polarize all NMR components fully in which case the term $$\left(1 - e^{-\frac{TW_{ET}}{R \cdot T2_k}}\right)$$

in the equation for $EET_i$ is 1 and can be omitted. The parameter R requires optimization in the JI routine. It is a measure of the T1/T2 of the formation (and in addition, as will be seen later, can be a motion artifact detector). In other words, R is not calculated directly as T1/T2, but rather is fitted to the echo train data by being optimized by the JI routine. Echo trains and trainlets may have different interecho times TE. The long echo train and averaged trainlets need weighting according to their number of averages, which is equivalent to the squares of their inverted measurement errors (see REF1).

In separate inversion (SI), the averaged echo trains are inverted (i.e., multiexponential fit) giving an echo train T2 distribution. The averaged trainlets are inverted (separate from the echo trains, hence the name SI) giving a trainlet T2 distribution. The principle for producing the final T2 distribution is by replacing in the echo train T2 distribution the short-T2 components by the short-T2 components of the trainlet T2 distribution. REF1 describes the details, including small modifications to improve the accuracy e.g. by the method of Chen and Georgi 1997.

Next, motion artifacts are discussed. Movement of an NMR tool, during the sampling or receiving of the NMR echoes, might cause motion artifacts in the decay of the long echo train and to a smaller degree in the trainlets. The main motion artifact is a reduction of FF components in the T2 distribution. What is lost from the FF component is then mainly found in an increase of the BW component. Looking alone at the long echo train, it is not possible to decide whether the BW component (or part of it) is really BW or a motion artifact.

When inverting long echo trains with long wait time combined with the trainlets with short wait time using the prior art inversion methods (such as REF1), the fitted T2 decays either do not fit perfectly to both types of echo trains, or R=T1/T2 is fitted unrealistically high if both echo train types were subjected to the same motion. As disclosed herein, this misfit is used to detect and correct motion artifacts in the NMR data. The disclosed inversion methods can find motion artifacts and remove or at least reduce them resulting in more accurate NMR data and more accurate formation property values derived from the corrected NMR data.

Figure 2:
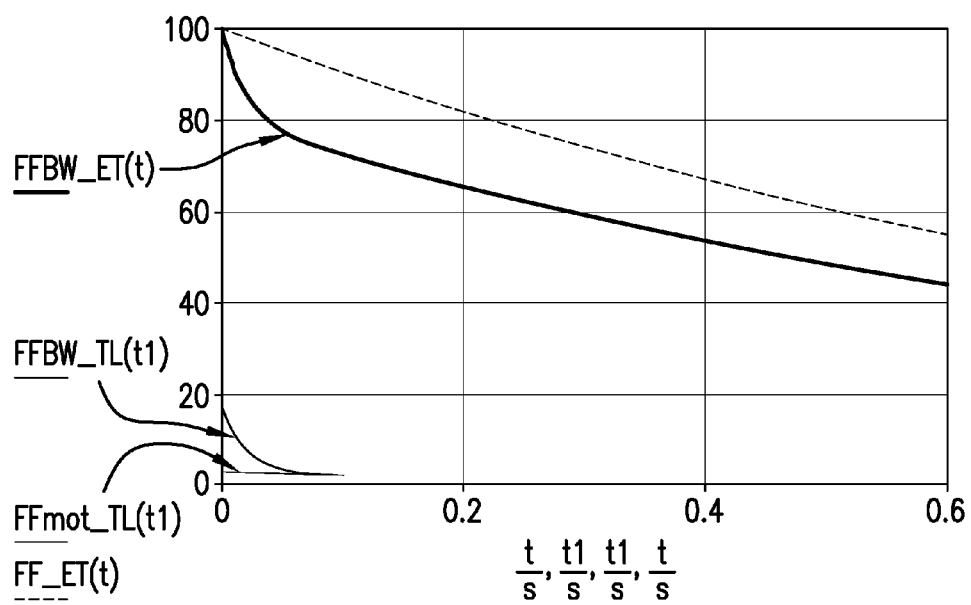
FIG. 2 depicts aspects of idealized NMR echo trains and idealized trainlets for illustration of an NMR motion artifact.

Next, manifestations of motion artifacts in NMR echo trains are discussed with reference to FIG. 2. Such a motion artifact as illustrated in FIG. 2 can only occur if free fluid (FF) is present in the formation, when some of the fractional porosity of the FF is converted by the motion to a fractional porosity with apparent T2 in the region of BW. FIG. 2 illustrates these ideas. In FIG. 2, the horizontal axis is the time axis[s] and the vertical axis is the NMR amplitude. A measured NMR echo decay might look like trace FFBW_ET (except for the lack of noise). From this echo train alone, it cannot be decided whether the fast decay at the beginning of that echo train is due to bound water (BW) content of 20% and the remainder a free fluid (FF) content of 80% or whether the BW is not real and in fact a motion artifact. In the latter case, the real FF would be 100% (trace FF_ET). It can be seen that the appearance of the trainlets allows motion artifacts to be distinguished from true bound water. Observe the two trainlet traces in the bottom left of the diagram for which the wait time (i.e. polarization time) is short so that the FF component is polarized to a small degree only. Trace FFBW_TL shows how the trainlet would look if the NMR sample was composed of 80% free fluid (FF) and 20% BW. The FF content is nearly fully suppressed by the short TW while the BW content is preserved with only a little attenuation. Trace FFmot_TL shows how the trainlet would look if the NMR sample was composed of 100% FF and the fast decay at the beginning of trace FFBW_ET was a motion artifact. In this case, the trainlet trace would be, as shown, a scaled-down version of the early times of trace FFBW_ET. Hence, by comparing the shape of the trainlet to the shape of the corresponding beginning portion of the long echo train, it can be determined if that portion is due to BW or a motion artifact. In one or more embodiments, BW and a motion artifact may be present at the same time. In such a case it may be challenging to identify by eye a motion artifact. Instead an algorithm may be used as described further down in this description.

Fortunately, it does not matter much whether the motion that was present during the long-TW echo train is or is not present during the trainlets. This is because the trainlets anyway show very little motion artifacts as the motion artifacts considered here can only be generated in the presence of FF NMR signals; yet FF NMR signals are very much suppressed in the trainlets with their short TW.

This concept is applicable if the motion artifact in the long-TW echo train looks similar to a fast decaying bound water component. This is generally the case if the artifact is caused by eccentric rotation of an axisymmetric NMR tool or by centric rotation when its magnetic field is not perfectly axi-symmetric. If the motion starts later in the echo train (such as by a sudden shock), the motion artifact is less of a problem because it is less likely to be mistaken for a wrong BW component.

Next, joint inversion with motion artifact correction (JIMC) is discussed. The two fit-able equations (1) presented above are modified with an additional multiplicative term, fitting the motion effect. A possible term is $$1 - Amot \cdot \left(1 - e^{-\frac{t}{Tmot}}\right)$$

with Amot and Tmot being the severeness (amplitude) and characteristic transient time of the motion artifact, respectively. The complete set of fitable equations for the T2 inversion is now:

$$EET_i = (1 - Amot \cdot (1 - e^{-\frac{t_i}{Tmot}})) \cdot \sum_k \left(\phi_k \cdot e^{-\frac{t_i}{T2_k}}\right) \qquad (2)$$

-continued $$ETL_j = \left(1 - Amot \cdot \left(1 - e^{-\frac{t_j}{Tmot}}\right)\right) \cdot \sum_k \left(\phi_k \cdot e^{-\frac{t_j}{T2_k}} \cdot \left(1 - e^{-\frac{TW_{TL}}{R \cdot T2_k}}\right)\right)$$

where R=T1/T2 requires optimization in the joint inversion routine and the long echo train and averaged trainlets need weighting according to their number of averages which is equivalent to the squares of their inverted measurement errors (see REF1). In the first equation it is assumed that the wait time $TW_{ET}$ is long enough to polarize the NMR nuclei fully. If this was not the case, then an appropriate recovery term needs adding as in equations (1). The new parameters are Amot and Tmot. The unknowns are: $\phi_k$, R=T1/T2, Amot and Tmot. It is useful to constrain these fitable parameters to real values ≥0. This may be done, for example, by substituting the squares of the square roots of these parameters in the equations before the fitting or by some other means. In one or more embodiments, R is constrained to be greater than one and Amot is constrained to be between zero and one.

In the above fitting equations (2), it is assumed that the same motion is present during the long-TW echo train and the short-TW trainlet. In reality, this is not necessarily the case but should be of minor consequence because the trainlets show very little FF signal and therefore in the trainlets not much FF can be converted to BW by the motion.

Next, joint inversion with motion correction using a long echo train and two trainlet types is discussed. The system of equations (2) can be extended for one echo train with full polarization and two trainlets with different wait times $TW_{TL1}$ and $TW_{TL2}$. The complete set of fitable equations for the T2 inversion then becomes:

$$EET_i = \left(1 - Amot \cdot \left(1 - e^{-\frac{t_i}{Tmot}}\right)\right) \cdot \sum_k \left(\phi_k \cdot e^{-\frac{t_i}{T2_k}}\right) \quad (3)$$

$$ETL1_{j1} = \left(1 - Amot \cdot \left(1 - e^{-\frac{t_{j1}}{Tmot}}\right)\right) \cdot \sum_k \left(\phi_k \cdot e^{-\frac{t_{j1}}{T2_k}} \cdot \left(1 - e^{-\frac{TW_{TL1}}{R \cdot T2_k}}\right)\right)$$

$$ETL2_{j2} = \left(1 - Amot \cdot \left(1 - e^{-\frac{t_{j2}}{Tmot}}\right)\right) \cdot \sum_k \left(\phi_k \cdot e^{-\frac{t_{j2}}{T2_k}} \cdot \left(1 - e^{-\frac{TW_{TL2}}{R \cdot T2_k}}\right)\right)$$

It can be appreciated that this system of equations can be extended to any number of echo trains and trainlets. Trainlets with medium wait time TW (i.e., greater than short TW and less than long TW), or with two different TWs, are in particular useful for a realistic determination of the fitting parameter R, noting that a realistic determination of R is the precondition for obtaining a realistic fitting of the motion artifact.

It should be noted that the different echo trains of equations (2) and (3) do not need to have the same interecho time TE. These equations can be used with echo trains with different numbers of echoes NE and different interecho times TE.

Next, examples of applying the joint inversion with motion artifact correction are presented. These examples are based on simulated NMR echo decays with simulated motion artifacts. For this section, the parameters are: FF are T2 components greater than 100 ms, BW are T2 components between 3.3 millisecond (ms) and 100 ms, and CBW are T2 components less than 3.3 ms.

A free fluid (FF) example is presented with one relaxation component of T2=1 sec. and R=T1/T2=1.5. The long echo train is fully polarized while the trainlets use a wait time of 60 ms and are weighted 96 times with $\sqrt{96}$ times lower noise. The prior art joint inversion (JI) is compared to the invented joint inversion with motion correction (JIMC).

Figure 3A:
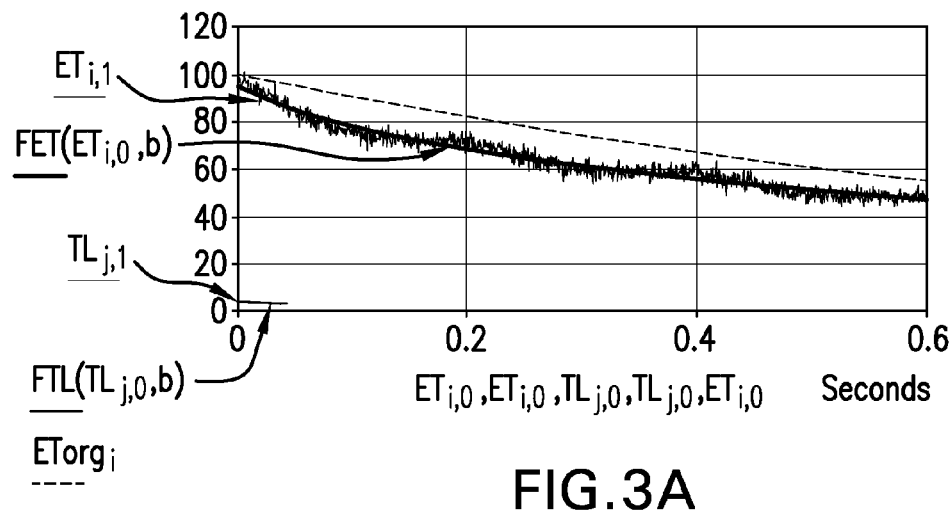
FIGS. 3A-3C, collectively referred to as FIG. 3, depict aspects an NMR echo train and trainlet used to demonstrate prior art joint inversion in the presence of a motion artifact.
Figure 3B:
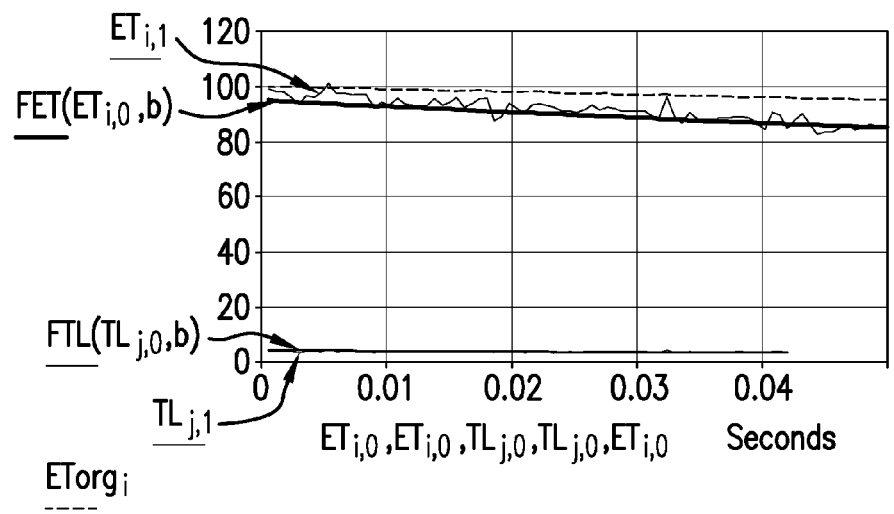
Figure 3C:
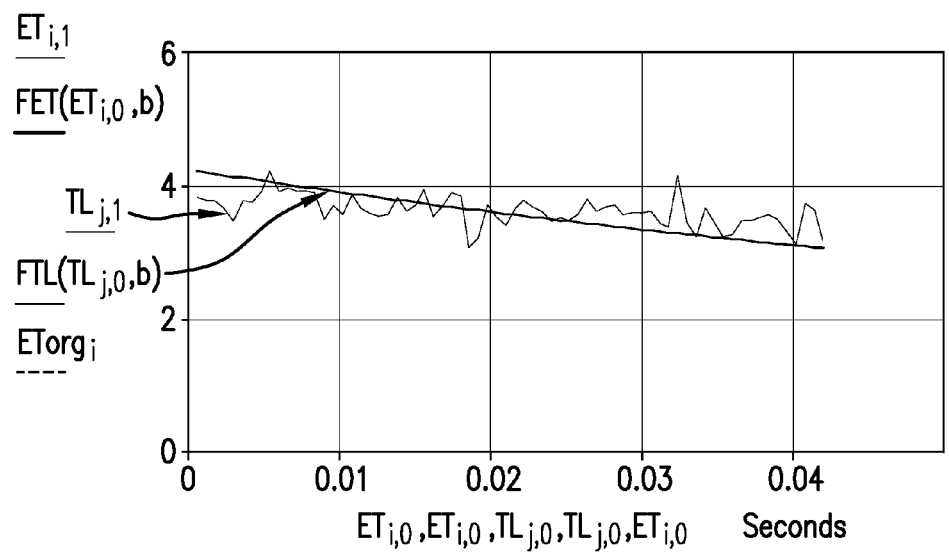
Figure 4:
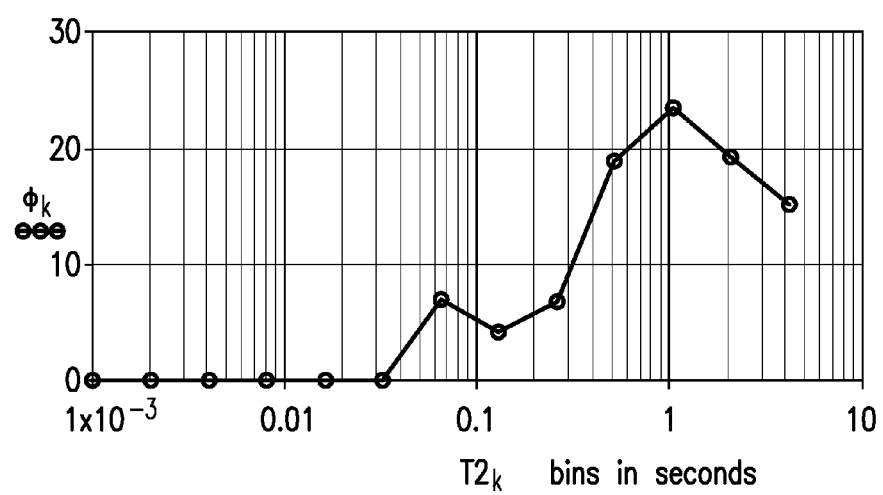
FIG. 4 depicts aspects of the $T_2$ distribution resulting from the prior art joint inversion.

FIG. 3 depicts aspects of an NMR echo train and trainlet used to demonstrate prior art joint inversion in the presence of a motion artifact. FIG. 3A illustrates a noisy simulated echo decay of 1000 echoes (ET) together with a trainlet (bottom left corner). The horizontal axis is the time axis with time in seconds. The vertical axis is the echo amplitude axis, normalized to 100% for the start of an echo train without artifact and noise and with full polarization. The dotted trace indicates an artifact-free mono-exponential decay with a characteristic decay time of 1 second—the expected noise free and motion artifact free echo decay. The deviation between noisy trace and the dotted trace is due to noise and motion artifact. The prior art joint inversion obtains the fits in the long echo train (trace FET) and in the trainlet (trace FTL). FIG. 3B shows FIG. 3A, but with the time axis magnified (i.e., zoomed in) to show the times 0 sec to 0.05 sec only. FIG. 3C is also a magnified view of FIG. 3A, but showing details of the trainlet TL with its fit FTL. It is seen in FIG. 3B that the fit (FET) of the inversion is systematically too low at the start of ET (which results in too low total porosity). Similarly, in FIG. 3C the fit FTL shows a systematic deviation (i.e., misfit) from the trainlet TL (i.e., wrong slope). (A motion corrected fit should find the true motion artifact-free echo decay ETorg.) The T2 distribution obtained by the prior art joint inversion is given in FIG. 4 in which the horizontal time bin axis is in seconds. The distribution of $\Phi_k$ in FIG. 4 provides a determination of certain properties:

Total porosity: 95.1% (true 100%);
FF: 88.0% (true 100%);
BW: 7.1% (true 0%);
CBW: 0.0% (true 0%); and
R=T1/T2: 3.2 (true 1.5).

Both, the R fitted unrealistically high, and the misfits in FIGS. 3B and 3C are indications of an incompatibility of the trainlets TL with the echo train ET with regards to data processing that does not comprise motion artifacts. While a misfit (systematic deviation from the data to be fitted) is either obvious or can be determined by an appropriate algorithm, an R fitted too high can be identified by comparing with a likely R for a particular formation type. (A JI with motion correction, i.e. JIMC, should find an R nearer to the true R.) A likely or reference R for a formation type may be determined by testing of an NMR tool in different formation types or by analysis so that the fitted R can be compared to the likely R. Hence, by knowing if the fitted R for a type of formation being drilled differs from the likely R by more than a threshold value, then an indication can be provided that the fitted R is incompatible with the NMR data.

Figure 5A:
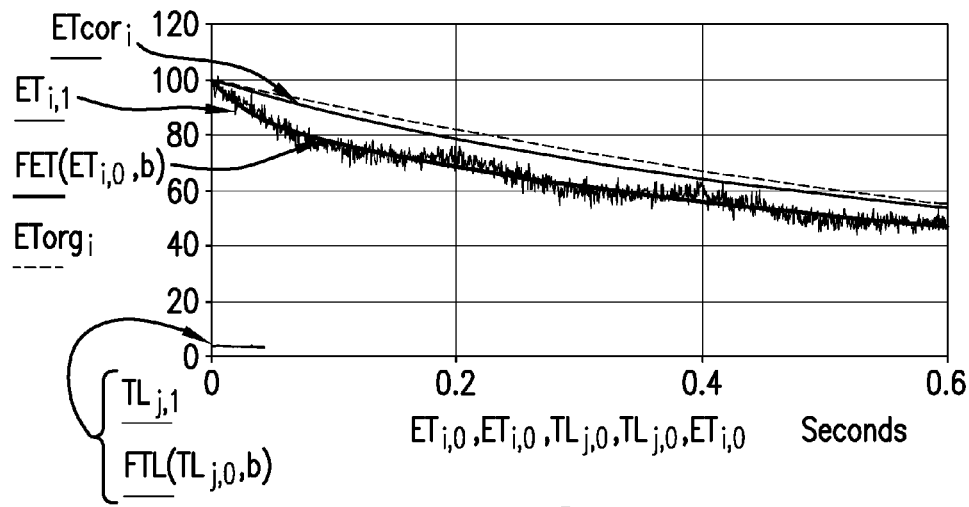
FIGS. 5A-5C, collectively referred to as FIG. 5, depict aspects of an NMR echo train and trainlet used to demonstrate joint inversion with motion correction.
Figure 5B:
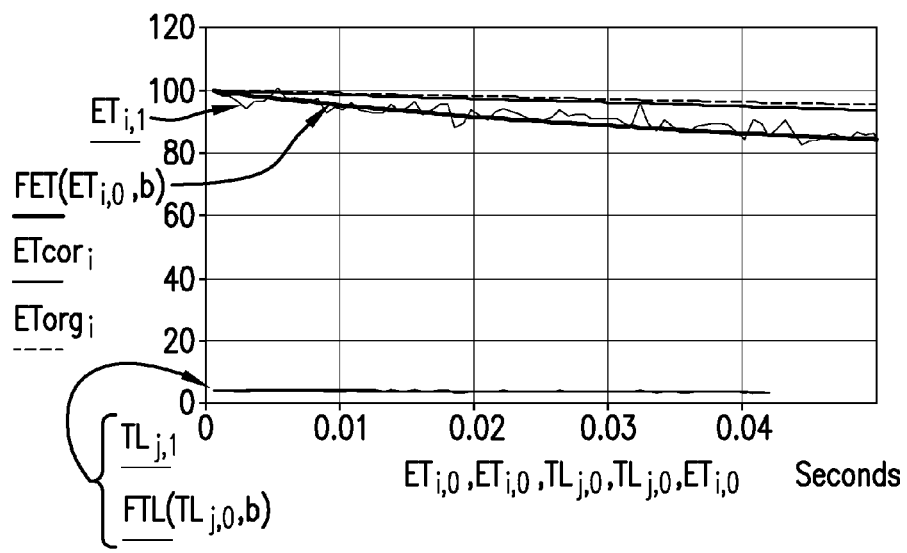
Figure 5C:
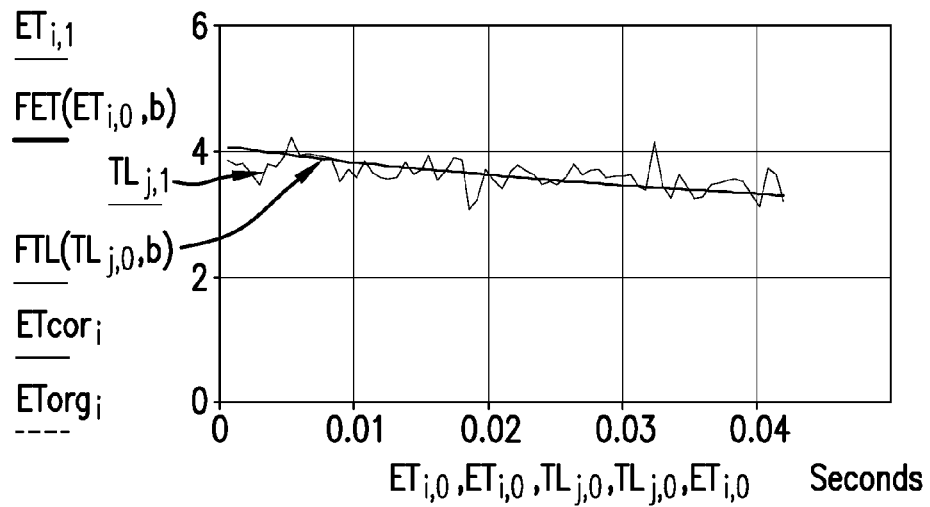
Figure 6:
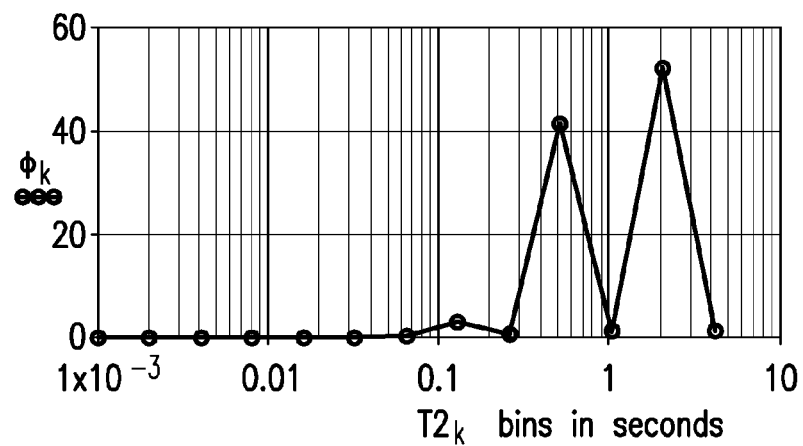
FIG. 6 depicts aspects of the $T_2$ distribution resulting from the joint inversion with motion correction.

FIG. 5 is similar to FIG. 3 and illustrates a noisy long echo train trace (ET) and a fit to this trace (FET) using JIMC. FIGS. 5B and 5C are magnified versions of FIG. 5A (in the same way that FIGS. 3B and 3C were magnified versions of FIG. 3A). The FET trace reproduces the total porosity at the start of the long echo train correctly (FIG. 5B) and the fit of the trainlet, FIG. 5C, is better than that of FIG. 3C. The resulting T2 distribution using JIMC is illustrated in FIG. 6. If the multi-exponential decay, generated from the above mentioned T2 distribution in FIG. 6, is plotted, the trace (ETcor) just below the dotted trace (ETorg) in FIGS. 5A and 5B is obtained. This is the motion corrected fit, which is not far from the artifact-free dotted trace, ETorg. The differences to the true T2 components are very small. The motion artifact is almost completely removed. The FF component with its two peaks in the T2 distribution may look irregular. This is because the JIMC of the equations (2) does not yet include a proper regularization. In one or more embodiments, such regularization would be used. The distribution of $\Phi_k$ in FIG. 6 provides a determination of certain properties:

Total porosity: 99.9% (true 100%);
FF: 99.7% (true 100%);
BW: 0.2% (true 0%);
CBW: 0.0% (true 0%);
R=T1/T2: 1.9 (true 1.5);
Amot: 0.13; and
Tmot: 0.033 s.

The estimates of these properties using JIMC are more accurate than the estimates using prior art JI in the above paragraph.

Figure 7:
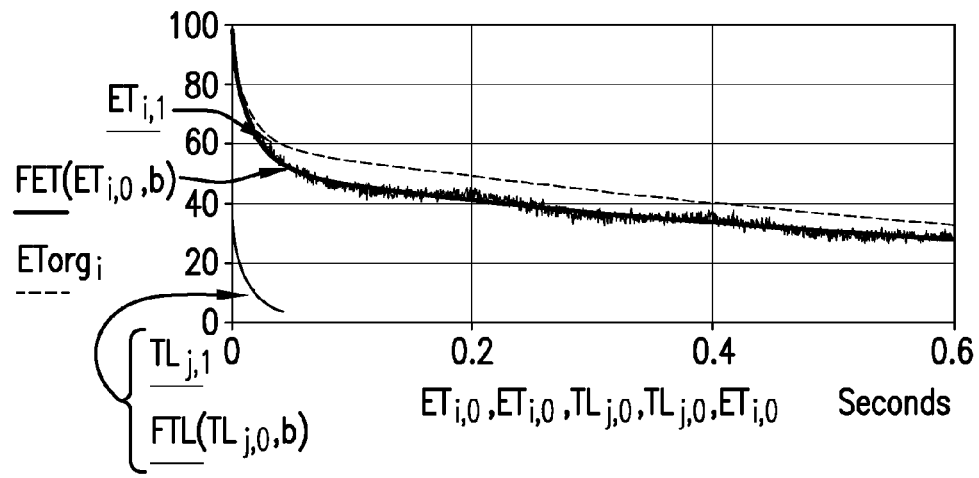
FIG. 7 depicts aspects of an NMR long echo train and trainlet with a short wait time of 60 ms used to demonstrate prior art joint inversion.
Figure 8:
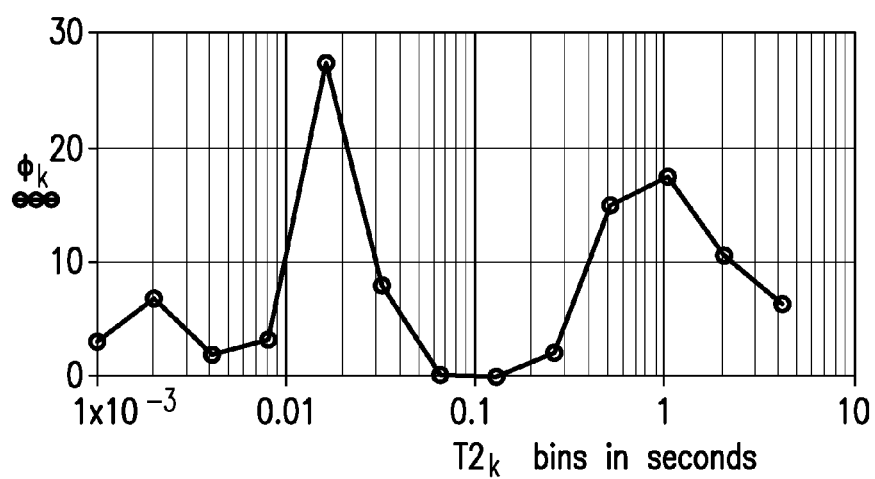
FIG. 8 depicts aspects of the $T_2$ distribution resulting from the prior art joint inversion of the NMR long echo train with long wait time and trainlet with the short wait time of 60 ms.

Another example using both JI and JIMC is presented with respect to characterizing shaly sand. This is a simulated example with three relaxation components: 60% FF with T2=1 s, 30% BW with T2=15 ms, 10% CBW with T2=1.5 ms and R=T1/T2=1.5 for all components. The long echo train is fully polarized while the trainlets use a wait time of 60 ms and are weighted 96 times with $\sqrt{96}$ times lower noise. The example further compares the output of JIMC using one or two trainlets. The figures used in this example are equivalent to the figures used in the free fluid example. FIGS. 7 and 8 relate to using the prior art JI with a long echo train and one trainlet with wait time TW=60 ms. The distribution of $\Phi_k$ in FIG. 8 provides a determination of certain properties:

| Total porosity: | 102.0% | (true 100%); |
| FF: | 51.6% | (true 60%); |
| BW: | 40.6% | (true 30%); |
| CBW: | 9.9% | (true 10%); and |
| R = T1/T2: | 2.7 | (true 1.5). |

Figure 9:
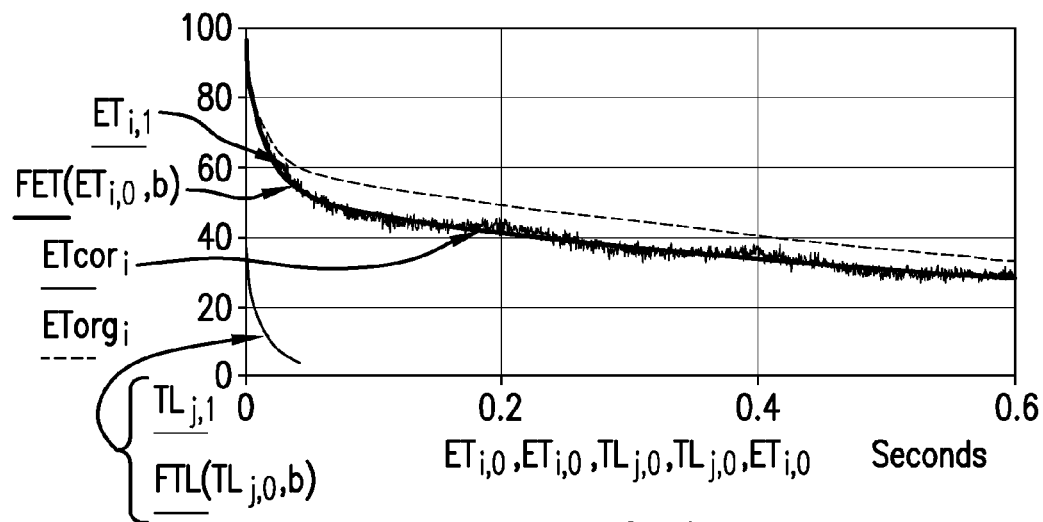
FIG. 9 depicts aspects of an NMR long echo train with long wait time and trainlet with a short wait time of 60 ms used to demonstrate joint inversion with motion correction.
Figure 10:
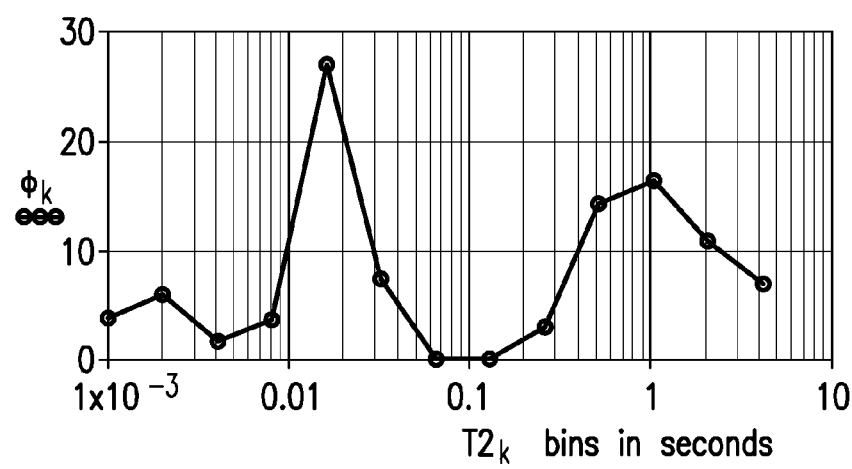
FIG. 10 depicts aspects of the $T_2$ distribution resulting from the joint inversion with motion correction of the NMR long echo train with long wait time and trainlet with the short wait time of 60 ms.

FIGS. 9 and 10 relate to using JIMC with a long echo train and one trainlet with wait time TW=60 ms. The distribution of $\Phi_k$ in FIG. 10 provides a determination of certain properties:

| Total porosity: | 102.0% | (true 100%); |
| FF: | 51.8% | (true 60%); |
| BW: | 40.2% | (true 30%); |
| CBW: | 9.9% | (true 10%); |
| R = T1/T2: | 2.6 | (true 1.5); |
| Amot: | 0.000004; and | |
| Tmot: | 0.131 s. | |

It is noted that in this example the accuracy using JIMC is comparable to the accuracy using the prior art JI (Amot is fitted to almost zero). However, a good fit is found with an excessive R=2.6. Because of the good fit, it is clear that not enough information for motion correction is contained in the long echo train and the trainlet for this example.

Figure 11:
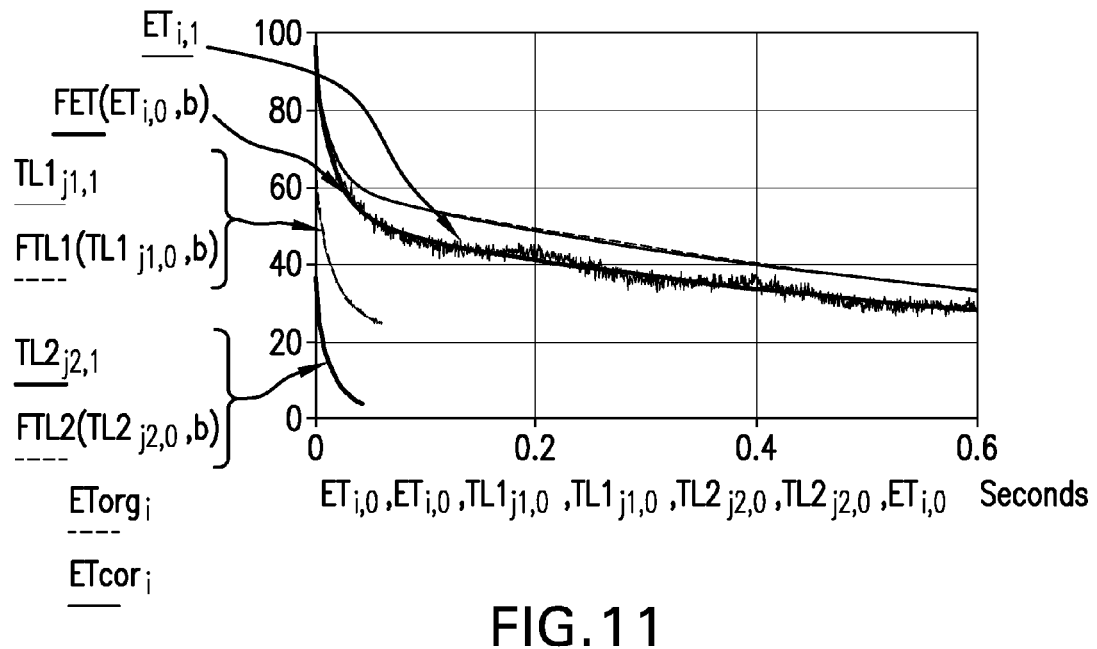
FIG. 11 depicts aspects of an NMR long echo train with long wait time and two trainlet types with different wait times (one second and 60 ms) used to demonstrate joint inversion with motion correction.
Figure 12:
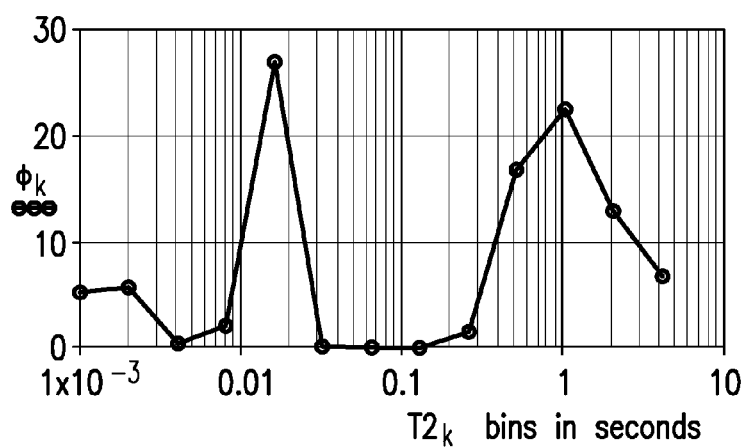
FIG. 12 depicts aspects of the $T_2$ distribution resulting from the joint inversion with motion correction of the NMR long echo train with long wait time and two trainlet types with different wait times (one second and 60 ms)

Because in the previous example there was not enough information in the long echo train and the trainlet, a second trainlet is added with a wait time TW=1 sec that is different to that of the first trainlet (TW=60 ms). FIGS. 11 and 12 relate to using JIMC with a long echo train, one trainlet with wait time TW=60 ms, and one trainlet with wait time TW=1 s. The distribution of $\Phi_k$ in FIG. 12 provides a determination of certain properties:

| Total porosity: | 101.0% | (true 100%); |
| FF: | 60.4% | (true 60%); |
| BW: | 29.7% | (true 30%); |
| CBW: | 10.9% | (true 10%); |
| R = T1/T2: | 1.4 | (true 1.5); |
| Amot: | 0.16; and | |
| Tmot: | 0.041 s. | |

In this example with two trainlets, the JIMC finds the correct R and the motion artifact and correctly removes the artifact. Further, looking at FIG. 11, it is seen that all fits derived from the T2 distribution of FIG. 12 and plotted in FIG. 11 (FET, FTL1, FTL2) are excellent. The FET trace in FIG. 11 is the result of the fitted equations (3) and fits the echo train with its artifacts. The ETcor trace in FIG. 11 is the corrected echo train, using the fitted T2 distribution and R in the first equation (EET) of equations (3) while leaving off the motion term, $$1 - Amot \cdot (1 - e^{-\frac{t_j}{Tmot}}).$$

The corrected echo train reproduces faithfully the original echo train without motion artifact or noise.

FIG. 13 presents tabled results of the above-presented examples. The last line shows that JIMC with two trainlets obtains approximately the correct T2 components, even in the more difficult case of Shaly Sand with the following properties: Total porosity=100%; CBW (0 to 3.3 ms)=10%; BW (3.3. to 100 ms)=30%; and FF (0.1 to 4 sec)=60%.

Embodiments of motion artifact correction, described in the foregoing description, are variants of the disclosed Joint Inversion with Motion artifact Correction (JIMC), which are modifications of the prior art Joint Inversion (JI). It is to be understood, though, that other embodiments, like variants of Separate Inversion with Motion artifact Correction (SIMC), which are modifications of the prior art Separate Inversion (SI), are well within the scope of this patent application.

Aspects of the process of correcting for a motion artifact when SI is used for inversion of T2 data (SIMC) are now discussed. In SIMC, the averaged echo trains are inverted giving an echo train T2 distribution. (It is assumed that there is a motion artifact in the echo train, which caused a too high amplitude of the short-T2 components and a too low amplitude of the long-T2 components.) Now a combined T2 distribution is produced by replacing in the echo train T2 distribution the short T2 components by the short T2 components of the trainlet T2 distribution (so far identical to SI). This combining reduces the motion artifact in the replaced short-T2 components but the long-T2 components have still too low amplitude and therefore the total porosity is too low, too. To reduce now the motion artifact in the long-T2 components of the distribution, the short-T2 components of the trainlet are summed and this sum subtracted from the summed short-T2 components of the echo train, resulting in a difference. Then, this difference is distributed across the long T2 components of the combined T2 distribution. This results in getting a final T2 distribution with motion-artifact-reduced short and long T2 components and more correct total porosity. The result may be improved by using the method of Chen and Georgi 1997 as described in REF1.

In the prior art SI the TW of the trainlets is often set quite short, just to polarize the CBW but not the BW. As very often the motion effects manifest themselves in the BW region, the SIMC, as described above, may not be efficient in reducing motion artifacts. Rather, needed in addition to the CBW trainlets with a TW just long enough to polarize CBW, are also BW trainlets with a TW long enough to polarize the BW components. The CBW trainlets are then used as in prior art SI while the BW trainlets are used for the motion artifact correction. The sequence of processing will then be: produce a combined T2 distribution by replacing in the echo train T2 distribution the CBW-T2 components by the CBW-T2 components of the CBW-trainlet T2 distribution and the BW-T2 components by the BW components of the BW-trainlet T2 distribution. If a motion artifact was present in the replaced BW-T2 components of the echo train, then this motion artifact is now reduced in the combined T2 distribution but the long T2 components have still too low amplitude and therefore the total porosity is too low, too. To reduce now the motion artifact in the long-T2 components of the distribution: the BW-T2 components of the BW trainlet are summed and this sum subtracted from the summed BW-T2 components of the echo train, resulting in a difference. Then this difference is distributed across the long T2 components of the combined T2 distribution. This results in getting a final T2 distribution with motion-artifact-reduced short and long T2 components and more correct total porosity. The result may again be improved by using the method of Chen and Georgi 1997 as described in REF1. It can be appreciated that some motion artifacts may not affect the BW T2 components but may affect the CBW T2 components or both. T2 components affected by motion artifacts in the CBW region may be corrected using techniques similar to the above described techniques for correcting motion artifacts in the BW region.

Figure 14:
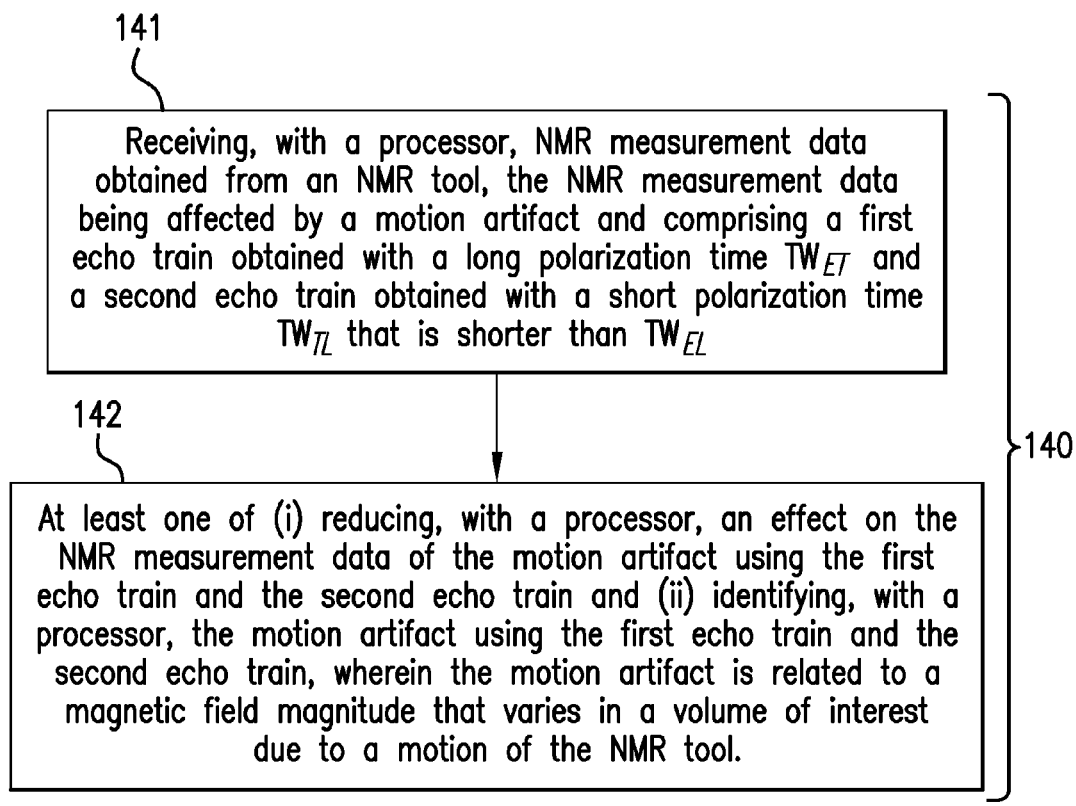
FIG. 14 is a flow chart for a method for estimating a property of an earth formation using NMR measurement data.

FIG. 14 is a flow chart for a method 140 for processing nuclear magnetic resonance (NMR) measurement data. Block 141 calls for receiving, with a processor, NMR measurement data obtained from an NMR tool, the NMR measurement data being affected by a motion artifact and comprising a first echo train obtained with a long polarization time $TW_{ET}$ and a second echo train obtained with a short polarization time $TW_{TL}$ that is shorter than $TW_{ET}$. Block 142 calls for at least one of (i) reducing, with a processor, an effect on the NMR measurement data of the motion artifact using the first echo train and the second echo train and (ii) identifying, with a processor, the motion artifact using the first echo train and the second echo train, wherein the motion artifact is related to a magnetic field magnitude that varies in a volume of interest due to a motion of the NMR tool. The motion may be due to at least one of radial movement, axial vibration, and rotation with non-axial symmetry of magnetic fields of the NMR tool. The NMR tool may be conveyed through a borehole penetrating an earth formation by a carrier such as a drill tubular.

Regarding the reducing in the method 140, reducing may include using a correcting inversion method that models the motion artifact to provide a corrected transverse relaxation time constant (T2) distribution. The correcting inversion may include using the following multiplicative term:

$$1 - Amot \cdot (1 - e^{-\frac{t}{Tmot}})$$

where Amot represents an amplitude of the motion artifact, Tmot represents a transient time constant of the motion artifact, and t represents time. The reducing may include using the equations (2) when the second echo train is a single echo train and equations (3) when the second echo train includes two echo trains.

Regarding the identifying in the method 140, identifying may include determining if multi-exponential approximations of T2 distributions of the first echo train and the second echo train obtained using a non-correcting inversion method that does not model the motion artifact provide an indication of incompatibility between the long echo train and the short echo train. The indication of incompatibility may be determined by a user who reviews the multi-exponential approximations and inputs into the identifying processor that there is an indication of incompatibility. In one example, the indication of incompatibility may exist when R is unreasonably high based on the details of the earth formation of interest. Equations (1) may be used for the multi-exponential approximations. Identifying may also include executing an algorithm that provides the indication of incompatibility. In one example of the algorithm, the algorithm may include equations (1). A motion artifact is indicated if either the joint fit of the two equations (1) is bad or the fitted R is excessively high. In another example of the algorithm, the algorithm may include equations (4).

$$EET_i = \sum_k \left( \phi E_k \cdot e^{-\frac{t_i}{T2_k}} \right) \qquad (4)$$

$$ETL_j = \sum_k \left( \phi T_k \cdot e^{-\frac{t_j}{T2_k}} \right)$$

For equations (4) when acquiring the $EET_i$ the polarization time is chosen to be long enough to substantially polarize FF and when acquiring the $ETL_j$ the polarization time is chosen to be long enough to substantially polarize BW but not FF. A motion artifact is then detected when the sum of those $\phi E_k$ that depend on BW is substantially greater than (e.g., greater by more than 10%) the sum of those $\phi T_k$ that depend on BW. The $\phi E_k$ and $\phi T_k$ that depend on BW are a subset of all the $\phi E_k$ and $\phi T_k$.

The method 140 may also include providing a corrected T2 distribution by reducing the effect of the motion artifact and then estimating a property of the earth formation using the corrected T2 distribution.

Motion artifact detection as well as motion artifact correction may be performed either downhole or uphole preferably in real time, or uphole when post processing the NMR data.

In support of the teachings herein, various analysis components may be used, including a digital and/or an analog system. For example, the downhole electronics 11, the computer processing system 12, or the NMR tool 10 may include digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

The flow diagrams depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first," "second" and the like do not denote a particular order, but are used to distinguish different elements.

While one or more embodiments have been shown and described, modifications and substitutions may be made thereto without departing from the spirit and scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for processing nuclear magnetic resonance (NMR) measurement data, the method comprising:
   conveying a downhole NMR tool through a borehole penetrating the earth and operating the downhole NMR tool in the borehole, the downhole NMR tool comprising a processor;
   receiving, with the processor, NMR measurement data obtained from the downhole NMR tool, the NMR measurement data being affected by a motion artifact and comprising a first echo train obtained with a long polarization time $TW_{ET}$ and a second echo train obtained with a short polarization time $TW_{TL}$ that is shorter than $TW_{ET}$;
   providing, with the processor, an indication of incompatibility between the first echo train and the second echo train;
   at least one of (i) reducing, with the processor, an effect on the NMR measurement data of the motion artifact using the first echo train and the second echo train using the indication of incompatibility and (ii) identifying, with the processor, the motion artifact using the first echo train and the second echo train using the indication of incompatibility; and
   applying motion correction, with the processor, on the NMR measurement data using the indication of compatibility;
   wherein the motion artifact is related to a magnetic field magnitude that varies in a volume of interest due to a motion of the NMR tool.

2. The method according to claim 1, wherein the motion of the NMR tool comprises at least one of radial movement, axial vibration, and rotation with non-axial symmetry of magnetic fields of the NMR tool.

3. The method according to claim 1, wherein reducing comprises using a correcting inversion method that models the motion artifact to provide a corrected transverse relaxation time constant (T2) distribution.

4. The method according to claim 3, wherein the correcting inversion method comprises the following multiplicative term:

$$1 - Amot \cdot (1 - e^{-\frac{t}{Tmot}})$$

where Amot represents an amplitude of the motion artifact, Tmot represents a transient time constant of the motion artifact, and t represents time.

5. The method according to claim 4, wherein the second echo train comprises one echo train and the correcting inversion method comprises the following equations:

$$EET_i = (1 - Amot(1 - e^{-\frac{t_i}{Tmot}})) \cdot \sum_k \left( \phi_k \cdot e^{-\frac{t_i}{T2_k}} \cdot \left(1 - e^{-\frac{TW_{ET}}{R \cdot T2_k}}\right) \right)$$

$$ETL_j = (1 - Amot(1 - e^{-\frac{t_j}{Tmot}})) \cdot \sum_k \left( \phi_k \cdot e^{-\frac{t_j}{T2_k}} \cdot \left(1 - e^{-\frac{TW_{ET}}{R \cdot T2_k}}\right) \right)$$

where $EET_i$ is the $i^{th}$ echo amplitude at time $t_i$ of the first echo train with a long wait time $TW_{ET}$, and $ETL_j$ is the $j^{th}$ echo amplitude at time $t_j$ of the second echo train with a short wait time $TW_{TL}$, $\phi_k$ represent amplitudes of exponential functions associated with chosen fixed $T2_k$ time interval bins with k running from 1 to a chosen number of T2 time interval bins, $T2_k$ representing a T2 time of the $T2_k$ time bin, and R represents T1/T2.

6. The method according to claim 5, wherein the term $$\left(1 - e^{-\frac{TW_{ET}}{R \cdot T2_k}}\right)$$

is estimated to be one.

7. The method according to claim 4, wherein the second echo train comprises two echo trains, ETL1 having wait time $TW_{TL1}$ and ETL2 having wait time $TW_{TL2}$, each of the second echo trains having a different wait time and the correcting inversion method comprises the following equations:

$$EET_i = (1 - Amot \cdot (1 - e^{-\frac{t_i}{Tmot}})) \cdot \sum_k \left(\phi_k \cdot e^{-\frac{t_i}{T2_k}} \cdot \left(1 - e^{-\frac{TW_{ET}}{R \cdot T2_k}}\right)\right)$$

$$ETL1_{j1} = (1 - Amot \cdot (1 - e^{-\frac{t_{j1}}{Tmot}})) \cdot \sum_k \left(\phi_k \cdot e^{-\frac{t_{j1}}{T2_k}} \cdot \left(1 - e^{-\frac{TW_{TL1}}{R \cdot T2_k}}\right)\right)$$

$$ETL2_{j2} = (1 - Amot \cdot (1 - e^{-\frac{t_{j2}}{Tmot}})) \cdot \sum_k \left(\phi_k \cdot e^{-\frac{t_{j2}}{T2_k}} \cdot \left(1 - e^{-\frac{TW_{TL2}}{R \cdot T2_k}}\right)\right)$$

where $EET_i$ is the $i^{th}$ echo amplitude at time $t_i$ of the first echo train with a long wait time $TW_{ET}$, $ETL1_{j1}$ is the $j1^{th}$ echo amplitude at time $t_{j1}$ of one of second echo trains with a short wait time $TW_{TL1}$, $ETL2_{j2}$ is the $j2^{th}$ echo amplitude at time $t_{j2}$ of the other second echo train with a short wait time $TW_{TL2}$, $\phi_k$ represent amplitudes of exponential functions associated with chosen fixed $T2_k$ time interval bins with k running from 1 to a chosen number of T2 time interval bins, $T2_k$ representing a T2 time of the $T2_k$ time bin, and R represents T1/T2.

8. The method according to claim 7, wherein the term $$\left(1 - e^{-\frac{TW_{ET}}{R \cdot T2_k}}\right)$$

is estimated to be one.

9. The method according to claim 1, wherein correcting comprises using Separate Inversion with Motion artifact Correction (SIMC).

10. The method according to claim 1, wherein identifying comprises determining if multi-exponential approximations of T2 distributions of the first echo train and the second echo train obtained using a non-correcting inversion method that does not model the motion artifact provide an indication of incompatibility between the long echo train and the short echo train.

11. The method according to claim 10, wherein the indication of incompatibility is input into the identifying processor by a user upon reviewing the multi-exponential approximations.

12. The method according to claim 11, wherein the user provides the indication of incompatibility when R exceeds a threshold value.

13. The method according to claim 11, further comprising inputting into the reducing processor instructions to use a correcting inversion method that models the motion artifact to provide a corrected transverse relaxation time constant (T2) distribution.

14. The method according to claim 10, wherein the multi-exponential approximations using the non-correcting inversion method are determined by using the following equations:

$$EET_i = \sum_k \left(\phi_k \cdot e^{-\frac{t_i}{T2_k}} \cdot \left(1 - e^{-\frac{TW_{ET}}{R \cdot T2_k}}\right)\right)$$

$$ETL_j = \sum_k \left(\phi_k \cdot e^{-\frac{t_j}{T2_k}} \cdot \left(1 - e^{-\frac{TW_{TL}}{R \cdot T2_k}}\right)\right)$$

where $EET_i$ is the $i^{th}$ echo amplitude at time $t_i$ of the first echo train with a long wait time $TW_{ET}$, $ETL_j$ is the $j^{th}$ echo amplitude at time $t_j$ of the second echo train with a short wait time $TW_{TL}$, $\phi_k$ represent amplitudes of exponential functions associated with chosen fixed $T2_k$ time interval bins with k running from 1 to a chosen number of T2 time interval bins, $T2_k$ representing a T2 time of the $T2_k$ time bin, and R represents T1/T2.

15. The method according to claim 14, wherein the indication of incompatibility is input into the identifying processor by a user upon reviewing the multi-exponential approximations and the user provides the indication of incompatibility when R exceeds a threshold value for a type of formation being logged or has a fit of the NMR data that exceeds a quantitative fit error value.

16. The method according to claim 10, further comprising executing an algorithm that provides the indication of incompatibility.

17. The method according to claim 16, wherein the algorithm comprises the following equations for the non-correcting inversion method:

$$EET_i = \sum_k \left(\phi E_k \cdot e^{-\frac{t_i}{T2_k}}\right)$$

$$ETL_j = \sum_k \left(\phi T_k \cdot e^{-\frac{t_j}{T2_k}}\right)$$

where $EET_i$ is the $i^{th}$ echo amplitude at time $t_i$ of the first echo train with a long wait time $TW_{ET}$, $ETL_j$ is the $j^{th}$ echo amplitude at time $t_j$ of the second echo train with a short wait time $TW_{TL}$, $\phi E_k$ and $\phi T_k$ represent amplitudes of exponential functions associated with chosen fixed $T2_k$ time interval bins with k running from 1 to a chosen number of T2 time interval bins, $T2_k$ representing a T2 time of the $T2_k$ time bin, and R represents T1/T2; and where $TW_{ET}$ is long enough to substantially polarize free fluid and $TW_{TL}$ is long enough to substantially polarize bound water and short enough to substantially not polarize free fluid components of a formation.

18. The method according to claim 17, wherein the algorithm provides the indication of incompatibility when the sums of those $\phi E_k$ that depend on the bound water or clay bound water components are substantially greater than the sums of those $\phi T_k$ that that depend on the bound water or clay bound water components.

19. A method for performing nuclear magnetic resonance (NMR) measurements on an earth formation, the method comprising:
conveying a downhole NMR tool through a borehole penetrating the earth formation and operating the downhole NMR tool in the borehole, the downhole NMR tool comprising a processor;
receiving, with the processor, NMR measurement data obtained from the NMR tool disposed on a carrier, the NMR measurement data being affected by a motion artifact and comprising a first echo train obtained with a long polarization time $TW_{ET}$ and a second echo train obtained with a short polarization time $TW_{TL}$ that is shorter than $TW_{ET}$;
providing, with the processor, an indication of incompatibility between the first echo train and the second echo train;
at least one of (i) reducing, with a processor, an effect on the NMR measurement data of the motion artifact using the first echo train and the second echo train using the indication of incompatibility and (ii) identifying, with a processor, the motion artifact using the first echo train and the second echo train using the indication of incompatibility;
applying motion correction, with the processor, on the NMR measurement data to generate motion corrected NMR measurement data using the indication of compatibility; and
estimating, with the processor, at least one of a T2 distribution, a total porosity, a fractional porosity, a pore size, and a fluid type using the motion corrected NMR measurement data;
wherein the motion artifact is related to a magnetic field magnitude that varies in a volume of interest due to a motion of the NMR tool.

20. The method according to claim 19, wherein the effect of the motion artifact is reduced to provide a corrected T2 distribution and the method further comprises estimating a property of the earth formation using the corrected T2 distribution.

21. The method according to claim 20, wherein the NMR tool is coupled to a carrier configured to be conveyed through the borehole.

22. The method according to claim 21, wherein the carrier is a drill tubular.

* * * * *